US009746446B2

(12) United States Patent
Faucher

(10) Patent No.: US 9,746,446 B2
(45) Date of Patent: Aug. 29, 2017

(54) PROBE HOLDER PROVIDING CONSTANT LIFT-OFF FOR IN-LINE BAR-PIPE TESTING

(71) Applicant: Denis Faucher, Quebec (CA)

(72) Inventor: Denis Faucher, Quebec (CA)

(73) Assignee: OLYMPUS SCIENTIFIC SOLUTIONS AMERICA INC., Waltham, MA (US)

( * ) Notice: Subject to any disclaimer, the term of this patent is extended or adjusted under 35 U.S.C. 154(b) by 285 days.

(21) Appl. No.: 14/814,943

(22) Filed: Jul. 31, 2015

(65) Prior Publication Data

US 2017/0030867 A1  Feb. 2, 2017

(51) Int. Cl.
*G01N 29/04* (2006.01)
*G01N 29/26* (2006.01)
*G01N 27/90* (2006.01)
*G01N 29/06* (2006.01)
*G01N 29/265* (2006.01)
*G01N 29/22* (2006.01)
*G01N 27/82* (2006.01)

(52) U.S. Cl.
CPC ....... *G01N 29/225* (2013.01); *G01N 27/9093* (2013.01); *G01N 29/041* (2013.01); *G01N 29/06* (2013.01); *G01N 29/262* (2013.01); *G01N 29/265* (2013.01); *G01N 27/82* (2013.01); *G01N 2291/0289* (2013.01); *G01N 2291/2634* (2013.01)

(58) Field of Classification Search
CPC .. G01N 27/9093; G01N 29/06; G01N 29/225; G01N 29/265; G01N 29/041; G01N 29/262; G01N 2291/0289; G01N 27/82; G01N 2291/2634

USPC ........................................................... 73/618
See application file for complete search history.

(56) References Cited

U.S. PATENT DOCUMENTS

| 3,986,390 A * | 10/1976 | Berner | G01N 29/24 73/634 |
| 5,122,740 A * | 6/1992 | Cottam | G01P 1/026 310/168 |
| 5,311,785 A * | 5/1994 | Bar-Shay | B29C 47/0023 73/622 |
| 6,341,525 B1 * | 1/2002 | Takada | B24B 27/033 73/584 |

FOREIGN PATENT DOCUMENTS

WO  WO2005108250  * 11/2005

* cited by examiner

*Primary Examiner* — J M Saint Surin
(74) *Attorney, Agent, or Firm* — C. Tricia Liu; Robert Kaim

(57) ABSTRACT

Disclosed is a probe holder for in-line inspection of the surface of bars of high value alloys. To attain full coverage of the inspected surface, the bar is rotated while either the bar or the probe holder is translated. The probe holder of the invention ensures constant probe lift-off by allowing the probe to move freely under its own weight, while constraining the motion to be only in the radial direction of the bar. The lift-off distance is defined by a spacer which is made of soft material to avoid damaging the inspected surface. Although the spacer is soft, its wear due to friction with the rotating bar is minimized by minimizing the pressure between the spacer and the bar. This is achieved by resting most of the mechanism weight on two rollers, with only the much smaller weight of the probe resting on the spacer.

20 Claims, 3 Drawing Sheets

PROBE HOLDER PROVIDING CONSTANT LIFT-OFF FOR IN-LINE BAR-PIPE TESTING

FIELD OF THE INVENTION

The invention relates to use of probes, such as eddy current or ultrasonic probes, for in-line non-destructive testing/inspection (NDT/NDI) of surface or near-surface flaws in bars of high value alloys.

BACKGROUND OF THE INVENTION

The term "in-line" refers to continuous NDT/NDI which occurs within the production line in which an alloy is produced or finished. Testing occurs continuously as the final product emerges from the production line, and its purpose is to ensure that the surface of the high value alloy is smooth, with no flaws, cracks or scratches. The bars to be inspected are generally cylindrical, the length of the axis of the cylinder usually being much larger than its diameter. Hereafter, a direction parallel to the axis of the bar will be referred to as an "axial" direction, and a direction perpendicular to the axis of the bar will be referred to as a "radial" direction. The bar cylinders may be comprised of solid material throughout, or they may be in the form of a tube or pipe with an outer diameter and an inner diameter. Testing is usually carried out by placing one or more probes close to the surface of the bar to be inspected, and then rapidly rotating the bar about its axis while translating either the bar or the probes in an axial direction. The purpose of the rotation and translation is to ensure that all parts of the surface to be tested pass sufficiently close to one or more probes so that flaws may be detected with sufficient sensitivity.

Use of eddy current probes for near-surface inspection is well known in the art. The probe may be in the form of a single coil, or there may be an array of coils placed at different orientations to enhance the sensitivity and efficiency of defect detection. The amplitude of the signal detected by a probe due to a defect is a sensitive function of the distance between the probe and the inspected surface. This distance is commonly referred to as the "lift-off" distance. In order to ensure that defects of the same type and size result in the same detected signal amplitude, it is essential to maintain constant lift-off at all times.

A significant difficulty in the prior art is maintaining constant lift-off under conditions of in-line testing, in which there is rapid and continuous relative movement between the probe and the inspected surface. The problem is exacerbated by the fact that the bar being tested is often not perfectly round and/or the rotation of the bar is eccentric. In either case, maintaining constant lift-off requires that the probe position needs to move rapidly back and forth in the radial direction as the bar rotates.

One prior art solution has been to employ a spacer between the probe and the surface, and to apply pressure on the spacer, often with the entire weight of the probe and mechanism assembly, or possibly by means of some other external force. The pressure ensures that the spacer always remains in intimate contact with the rotating surface, but the probe must be allowed to move in order to take account of the bar being out-of-round or the rotation being eccentric.

There are multiple problems with this prior art approach. If the spacer is made of hard material, then the pressure is liable to damage the inspected surface by causing scratches. On the other hand, if the spacer is made of soft material, then the high speed relative motion between the soft material and the alloy surface will result in rapid wear of the soft spacer. As the spacer wears down, the lift-off will change, resulting in detection errors until the spacer can be replaced during a maintenance procedure which will disrupt production.

Another problem with the prior art solutions is that the motion of the probe as the bar rotates needs to be accurately aligned with the radial direction of the bar. Any rotation of the probe, or translation parallel to the surface of the bar, will lead to defect detection errors.

Yet another problem with prior art solutions is that the probe holder is customized for a particular bar diameter. This means that the probe holder must be replaced and/or re-adjusted every time the bar size is changed, which is often a labor intensive operation resulting in costly disruption to production.

Yet another problem with prior art solutions is that the probe holder often does not allow the probe to be used in good alignment to the very end of a bar. This means that each bar will have an area at its ends which was not inspected for surface quality.

SUMMARY OF THE INVENTION

The purpose of the invention is to alleviate problems with prior art solutions. The invention is a probe holder assembly which comprises a frame, with two attached rollers and with mechanical links attaching a probe to the frame. The weight of the probe holder assembly rests on the rollers which are in contact with the surface of the bar to be inspected, and rotate in counter-rotation to the rotation of the bar. The mechanical links allow motion of the probe only in the radial direction of the bar, the radial direction being stably defined as perpendicular to the plane through the axes of the rollers in contact with the surface of the bar. The base of the probe, in close proximity to the eddy current coils, comprises a spacer which defines the lift-off distance. The spacer is made of soft material in order to avoid damaging the inspected surface, but since most of the weight of the probe holder assembly rests on the rollers, there is very little pressure between the spacer and the inspected surface, thereby avoiding excessive wear of the spacer. The spacer is long in the axial direction of the bar, which increases the surface area of the spacer, thereby further reducing the pressure between the spacer and the inspected surface. The rollers are also long in the axial direction thereby enabling the probe to be used in good alignment to the very end of a bar. The allowable range of motion of the probe in the radial direction is sufficient to allow inspection of bars with a wide range of diameters, without needing to make any adjustment to the probe holder assembly. The motion of the probe also serves to ensure that if the roller diameters change due to wear, the probe lift-off will not change.

It is a purpose of the present invention to maintain a constant lift-off distance utilizing a spacer made of soft material to avoid damaging the inspected surface.

It is a further purpose of the present invention to have the weight of the probe holder assembly resting on two rollers, with only the much lesser weight of the probe resting on the spacer, whereby the reduced pressure between the spacer and inspected surface reduces the wear on the spacer.

It is a further purpose of the present invention to have a spacer which is long in the axial direction, whereby the area of the spacer is increased, and the pressure between the spacer and inspected surface and the wear on the spacer are both further reduced.

It is a further purpose of the present invention to have the probe attached to the frame of the probe holder assembly by means of mechanical links which allow free movement of the probe only in the radial direction of the bar.

It is a further purpose of the present invention to have a probe holder which requires no adjustment or replacement when inspecting bars of different diameter.

It is a further purpose of the present invention to have a probe holder in which the lift-off is independent of any change of diameter of the rollers due to wear.

It is a further purpose of the present invention to have a probe holder in which the lift-off remains constant even if the tube is out-of-round or rotating eccentrically.

It is a further purpose of the present invention to have a probe holder which allows inspection to the very end of the bar.

DETAILED DESCRIPTION OF PREFERRED EMBODIMENT

Figure 1:
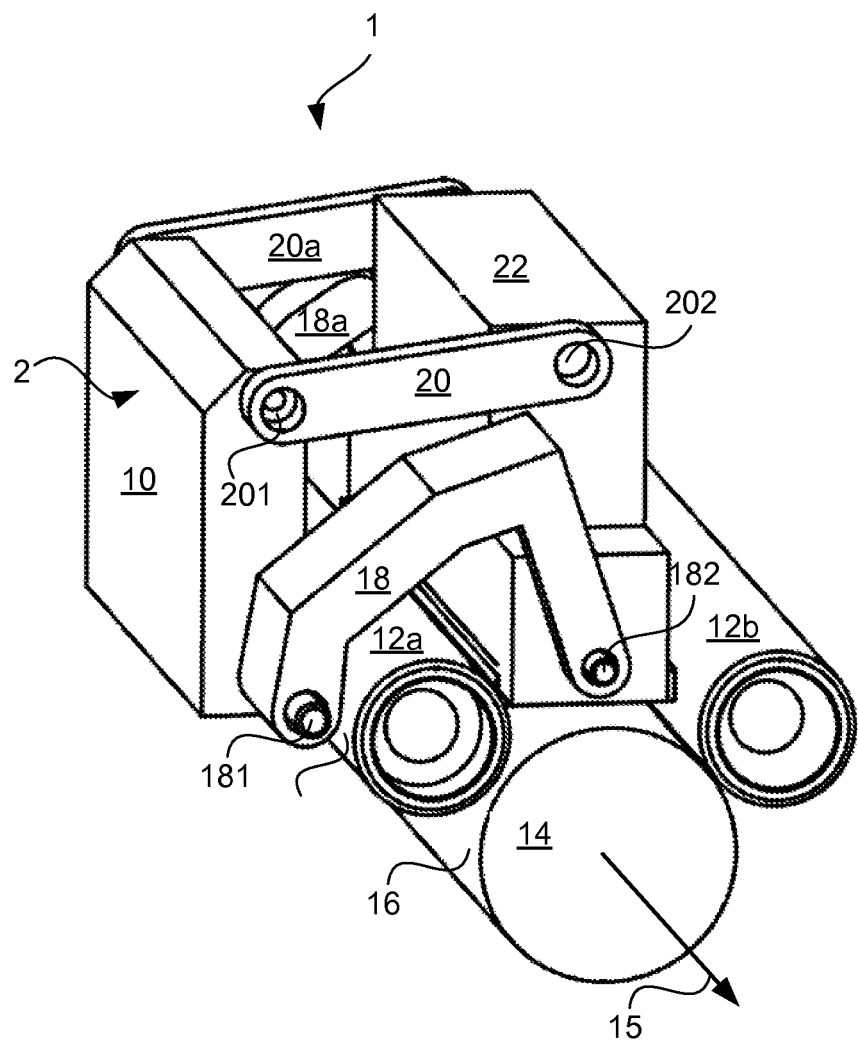
FIG. 1 is a schematic drawing of the probe holder and probe according to the present disclosure.

FIG. 1 shows a probe assembly 1 according to the present disclosure. Probe assembly 1 includes a probe 22 and a probe holder assembly 2. Probe holder assembly 2 comprises a frame 10, rollers 12a and 12b, and mechanical links 18, 18a, 20 and 20a. Mechanical links 18 and 18a are attached at one end to the frame 10 by means of freely rotatable pivot joints 181 and 181a (not shown), and at the other end to probe 22 by means of freely rotatable pivot joints 182 and 182a (not shown). Mechanical links 20 and 20a are attached at one end to the frame 10 by means of freely rotatable pivot joints 201 and 201a (not shown), and at the other end to the probe 22 by means of freely rotatable pivot joints 202 and 202a (not shown). Rollers 12a and 12b are generally cylindrical, and are attached to frame 10 such that they are free to rotate about their respective axes, but the axes are in fixed geometrical relation to frame 10. The outer surfaces of rollers 12a and 12b are in contact with outer surface 16 of a bar 14 which is being inspected, and the rollers 12a and 12b are free to rotate in counter-rotation to the rotation of the bar 14. An axial direction 15 is defined is being coincident with or parallel to the axis of cylindrical bar 14.

Still referring to FIG. 1, the mechanical links 18, 18a, 20 and 20a, and the freely rotatable pivot joints 181, 181a 182, 182a, 201, 201a, 202 and 202a, are designed so that probe 22 is free to move, but the motion is constrained to be linear and perpendicular to the plane through the axes of the two rollers. In a preferred embodiment, the probe holder is aligned so that the axes of the rollers are in a horizontal plane, in which case the motion of probe 22 is constrained to be vertical. However other orientations are possible and within the scope of the invention.

In the preferred embodiment, the entire weight of the probe holder rests on rollers 12a and 12b. Since the probe is free to move vertically, its weight will always ensure that the base of the probe rests on the surface 16 of the bar 14.

It should be noted that an important novel aspect of the present invention is having the weight of the probe holder assembly 2 separated from the weight of the probe 22. Another important novel aspect is that the weight of the probe holder assembly rests on rollers, not on the probe, while only the lesser weight of the probe rests on a spacer determining the lift-off distance, as later described in more detail in connection with FIG. 3. This allows for much more accurate and consistent lift-off distance, and avoids scratches on the test object caused by the heavy weight of the whole assembly.

Yet another very important novel aspect of the present disclosure is that the probe assembly allows free motion of the probe in the axial direction, thereby ensuring good contact with the inspected surface and constant lift-off throughout the inspection.

Continuing to refer to FIG. 1, during the inspection there is relative motion between probe assembly 1 and outer surface 16 of bar 14. Bar 14 may rotate, causing counter-rotation of rollers 12a and 12b. Alternatively, probe assembly 1 may move circumferentially around the surface of bar 14. Bar 14 may translate in the axial direction, causing a sliding motion between the surfaces of the rollers 12a and 12b and inspected surface 16. Alternatively, probe assembly 1 may translate in the axial direction. Any one or more of the above-mentioned motions, namely rotation of bar 14, axial translation of bar 14, circumferential motion of probe assembly 1 or axial translation of probe assembly 1, are within the scope of the present invention.

Note that the rollers 12a and 12b and the probe 22 are both long in the axial direction so that they may overlap the ends of the bar while still allowing stable alignment of the probe 22 relative to the bar 14. This ensures that the system is capable of inspecting the surface 16 all the way to each end of the bar 14.

Figure 2B:
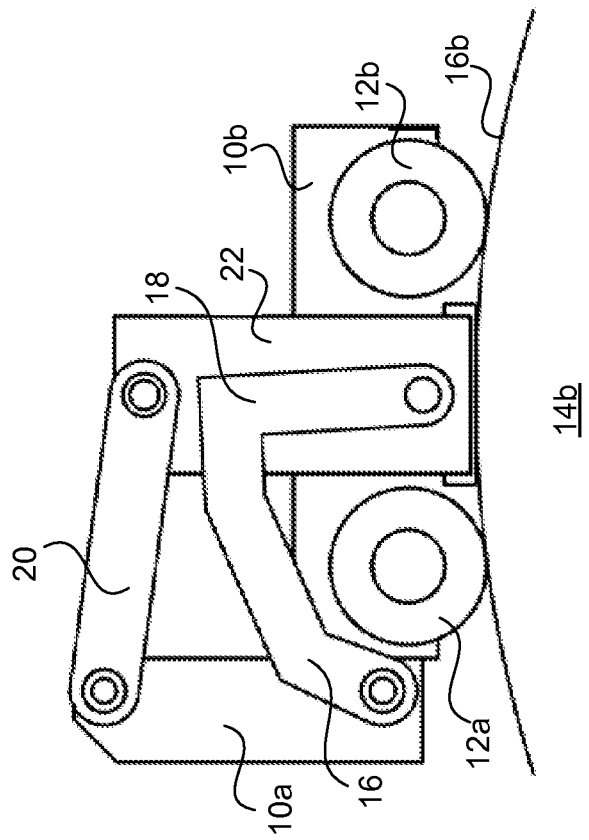
FIG. 2B is a schematic section view according to the present disclosure of the probe holder and probe during inspection of a bar of large diameter.
Figure 2A:
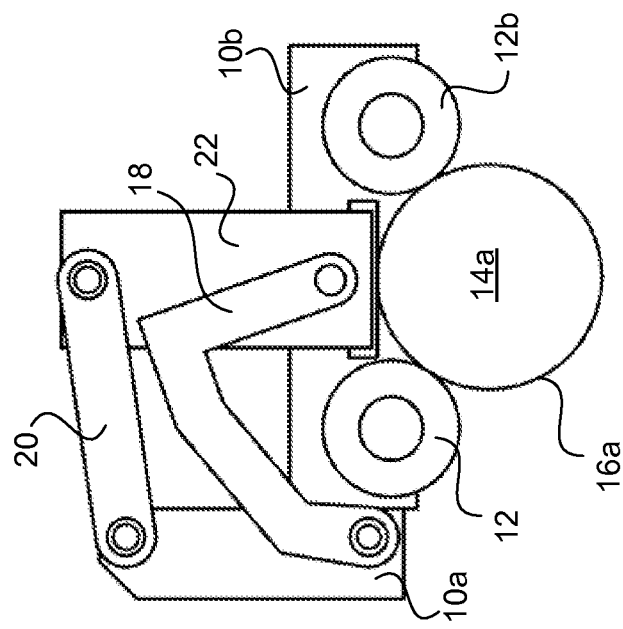
FIG. 2A is a schematic section view according to the present disclosure of the probe holder and probe during inspection of a bar of small diameter.

Turning now to FIG. 2A, there is shown a sectional view of probe holder assembly 2 and probe 22, while inspecting a bar 14a of small diameter. Note that in FIG. 2A, frame 10 is shown as consisting of two rigidly connected parts, 10a and 10b. Mechanical links 18, 18a, 20 and 20a are rotatably connected to frame 10a; the axes of rollers 12a and 12b are fixed to frame 10b, while still allowing rotation of the rollers about their respective axes. Also note that the surfaces of rollers 12a and 12b and the base of probe 22 are all in contact with surface 16a of bar 14a.

FIG. 2B shows a sectional view of probe holder assembly 2 and probe 22, while inspecting a bar 14b of large diameter. Only the upper part of bar 14b is shown in FIG. 2B. Note that the surfaces of rollers 12a and 12b and the base of probe 22 are all in contact with surface 16b of bar 14b. However, the orientation of mechanical links 18 and 20 is different in FIG. 2B from the orientation in FIG. 2A, allowing probe 22 to move downward to take account of the smaller curvature of the larger bar 14b. The downward motion of probe 22 occurs freely due to the weight of probe 22; there is no need to make any adjustment of the probe holder when changing from small diameter bar 14a to large diameter bar 14b. Moreover, in both FIG. 2A and FIG. 2B, the pressure between the base of probe 22 and surface 16b is due solely to the weight of probe 22. The larger weight of probe holder assembly 2 is supported by rollers 12a and 12b.

Figure 3:
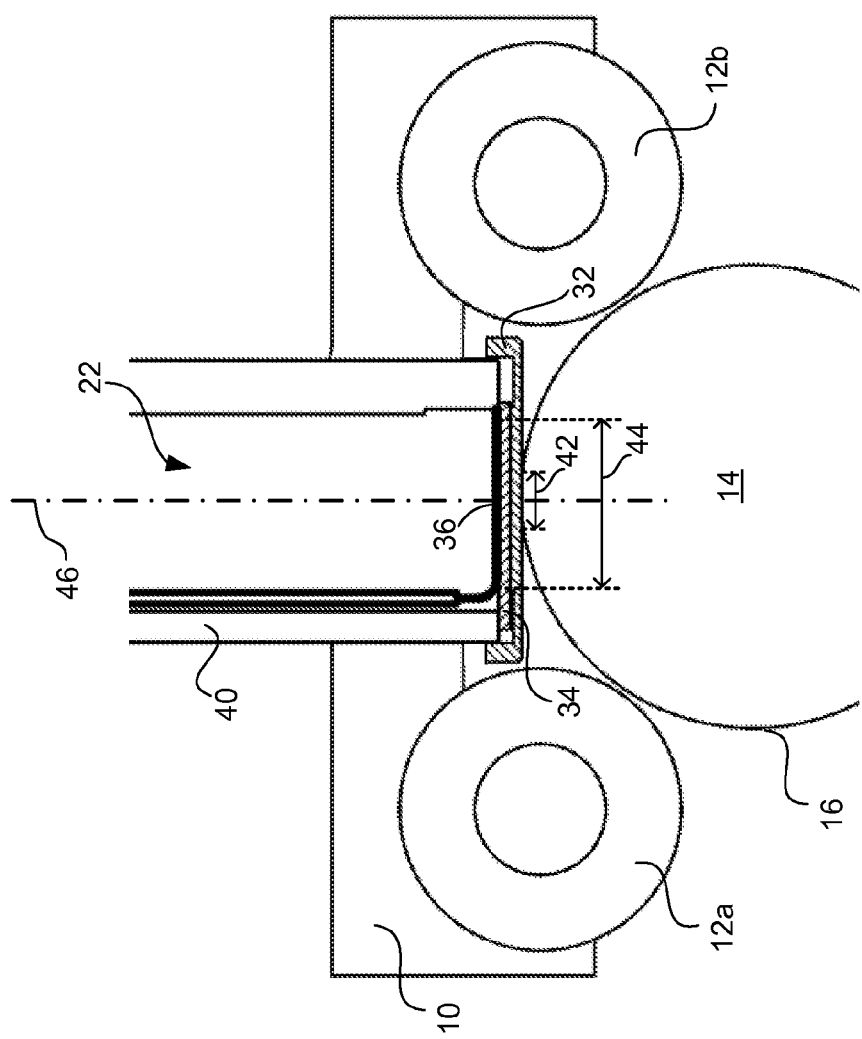
FIG. 3 is an enlarged view of the probe and rollers according to the present disclosure.

FIG. 3 shows an enlarged section view of the probe 22. Probe 22 has a geometric center line 46, and consists of an outer case 40, a coil assembly 36, a protective cap 34 and a soft spacer 32. In a preferred embodiment, the coil assembly 36 consists of an array of eddy current coils on a flexible printed circuit board which also includes electronic components for operation of the coils. However, the scope of the invention includes other kinds of probes, such as phased array ultrasonic probes, as well as any type of eddy current coils, including both single coils and coil arrays, in any configuration. In the present embodiment, the outer case 40 is open at its lower end, the end being closed off by protective cap 34 made of ceramic or some other protective non-magnetic material, and the active part of coil assembly 36, having a sensor area 44, is in close contact with protective cap 34. However, protective cap 34 may be omitted without departing from the scope of the present invention.

Soft spacer 32 is fixed to the lowest part of outer case 40 and is in contact with surface 16 of bar 14 over a contacting area 42. Contacting area 42 is the only part of probe 22 which is contact with surface 16. In a preferred embodiment, soft spacer 22 is made of HYDLAR Z aramid (Kevlar®) fiber filled composite, but any other suitable material may be used without departing from the scope of the invention.

Since probe 22 can move freely in the radial direction, it can move rapidly back and forth in response to eccentric rotation or out-of-roundness of the bar 14, while still maintaining constant contact between spacer 32 and the inspected surface 16.

It should be appreciated that the foregoing description is to disclose teaching, based on the exemplary embodiments, that allows the weight of the probe holder to rest on rollers, not on the probe, while only the lesser weight of the probe rests on the spacer determining the lift-off distance. The teaching also includes free motion of the probe in the axial direction, thereby ensuring good contact with the inspected surface and constant lift-off throughout the inspection. It can be appreciated that various designs can be conceived based on the teachings of the present disclosure, and are all within the scope of the present disclosure.

What is claimed is:

1. A probe assembly configured for conducting an operation of non-destructive testing and/or inspection (NDT/NDI) circumferentially around and on top of a testing surface of a cylindrical test object having an axial direction and a radial direction, the probe assembly comprising,
   a probe having a sensor area configured to glide over the testing surface, and with the sensor area being in close proximity to the testing surface at a contacting area during the operation,
   a probe holder assembly configured to hold the probe gliding over the testing surface causing the probe to be in a relative motion circumferentially around the testing object, wherein the probe holder assembly further comprises,
   at least one roller configured to roll on the testing surface in unison with the relative motion,
   a frame attached to the roller in a rigid manner during the operation,
   at least one mechanical link member attached to the frame and the probe in a manner allowing the probe to be carried by the probe holder assembly and to move in the radial direction substantially freely without transferring the weight of the frame to the probe.

2. The probe assembly of claim 1, wherein the relative motion corresponds to motion of the cylindrical test object, including rotation and/or axial translation, while the probe assembly remains substantially stationary.

3. The probe assembly of claim 1, wherein the relative motion corresponds to motion of the probe assembly, including circumferential motion and/or axial translation, while the cylindrical test object remains substantially stationary.

4. The probe assembly of claim 1, wherein the at least one linking member has a first linking means having a first two ends, the first two ends attached to the probe and the frame respectively via pivot joints.

5. The probe assembly of claim 4, wherein the first link member and the first two ends are configured so that the probe moves substantially freely in an axial direction which is perpendicular to the test surface, and substantially does not move relative to the test surface in any other direction.

6. The probe assembly of claim 4 wherein the at least one linking member has a second linking means having a second two ends, the second two ends attached to the probe and the frame respectively via pivot joints.

7. The probe assembly of claim 6 wherein the first linking means is attached to the probe at a first probe attaching position and the second linking means is attached at a second probe attaching position, wherein the first probe attaching position is higher than the second probe attaching position.

8. The probe assembly of claim 6, wherein the probe has a geometric center line, and wherein the first linking means and the second linking means are configured and attached to the probe so that the center line of the probe is maintained in a radial direction normal to the testing surface at all times as the probe glides over the test surface.

9. The probe assembly of claim 5, wherein the probe has a front end and a back end, and wherein the first linking means includes a pair of substantially identical first linking members, each of them attached to the front end and the back end of the probe respectively via pivot joints.

10. The probe assembly of claim 6, wherein the probe has a front end and a back end, and wherein the first linking means includes a pair of substantially identical first linking members, each of them attached to the front end and the back end of the probe respectively via pivot joints and the second linking means includes a pair of substantially identical second linking members, each of them attached to the front end and the back end of the probe respectively via pivot joints.

11. The probe assembly of claim 10 wherein the first linking means and the second linking means are both rigid.

12. The probe assembly of claim 1 wherein the at least one roller is a pair of rollers, each having a roller axis respectively, one on each side of the probe, wherein the rollers are attached to the frame via rigid attaching means, such that the two roller axes are parallel to the axial direction of the test object.

13. The probe assembly of claim 1, wherein the probe further comprises sensors and a spacer between the sensors and the testing surface, said spacer defining a lift-off distance between the sensors and the testing surface.

14. The probe assembly of claim 13, wherein the probe further comprises a protective cap located between the sensors and the spacer.

15. The probe assembly of claim 13, wherein the spacer is made of soft material which cannot scratch the testing surface, and wear on the spacer is minimized by minimizing the pressure between the spacer and the testing surface within the contacting area.

16. The probe assembly of claim 13, wherein the lift-off distance remains constant even as the diameter of the cylindrical roller changes due to wear.

17. The probe assembly of claim 5, wherein the probe assembly is used for NDT/NDI of test objects of different diameter, without need for any re-adjustment of the probe holder assembly.

18. The probe assembly of claim 5, wherein the probe can move rapidly back and forth in a radial direction in response to eccentric rotation or out-of-roundness of the test object, while the sensor area remains at all times in close proximity to the testing surface at the contacting area.

19. The probe assembly of claim 1, wherein the probe is an eddy current probe.

20. The probe assembly of claim 1, wherein the probe is a phased array ultrasonic probe.

* * * * *